United States Patent [19]

McGinnis et al.

[11] Patent Number: 5,658,245
[45] Date of Patent: Aug. 19, 1997

[54] THERAPEUTIC TENSION APPLYING TRAVEL AID APPARATUS ATTACHABLE TO A SEAT

[76] Inventors: Cathy D. McGinnis, 401 Canyon Way #43, Sparks, Nev. 89434; Andrew R. Hope, P.O. Box 1177, Captain Cook, Hi. 96704

[21] Appl. No.: 265,122

[22] Filed: Jun. 24, 1994

[51] Int. Cl.⁶ .................................................. A61F 5/00
[52] U.S. Cl. .............................. 602/32; 33/34; 33/35; 33/36; 33/40
[58] Field of Search ............................ 602/32, 33, 34, 602/35; 273/26 E, DIG. 30

[56] References Cited

U.S. PATENT DOCUMENTS

| | | | |
|---|---|---|---|
| 1,347,913 | 7/1920 | Rink | 602/32 X |
| 2,633,124 | 3/1953 | Yellin | 602/32 X |
| 2,633,125 | 3/1953 | Yellin | 602/32 X |
| 2,658,506 | 11/1953 | Haskell | 602/32 |
| 2,665,685 | 1/1954 | Kaufman | 602/32 |
| 2,984,238 | 5/1961 | Axtell et al. | 602/32 |
| 3,403,675 | 10/1968 | Carr | 602/32 |
| 3,695,256 | 10/1972 | Brower | |
| 3,750,658 | 8/1973 | Dawson, Jr. | |
| 3,759,255 | 9/1973 | Taylor | |
| 3,835,847 | 9/1974 | Smith | |
| 4,220,147 | 9/1980 | Allen | |
| 4,603,689 | 8/1986 | Horner | 128/75 |
| 4,869,240 | 9/1989 | Boren | 128/75 |
| 5,332,071 | 7/1994 | Duncan | 188/371 |

FOREIGN PATENT DOCUMENTS 1507373  9/1989  U.S.S.R. .................. 602/32

*Primary Examiner*—Richard J. Apley
*Assistant Examiner*—Kim M. Lee

[57] ABSTRACT

A therapeutic tension applying apparatus for applying tensile stress on a persons neck and spine while traveling, the apparatus is attachable to a vehicle seat or a mounting surface such as a ceiling within a vehicle. The apparatus provides adjustable, variable tension for the user and further includes a break-away-means which allows detachment of the apparatus from a chin strap or pad so as not to endanger the user, such as in the case of an accicent.

2 Claims, 3 Drawing Sheets

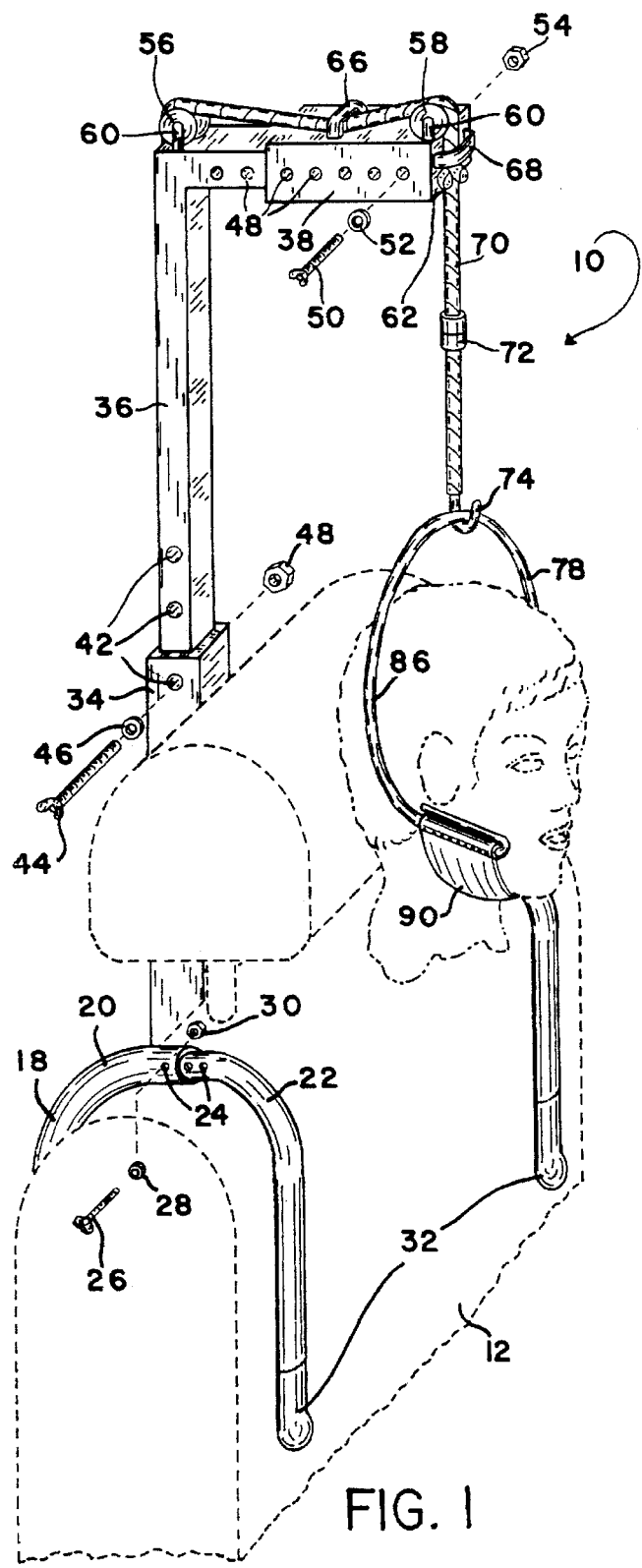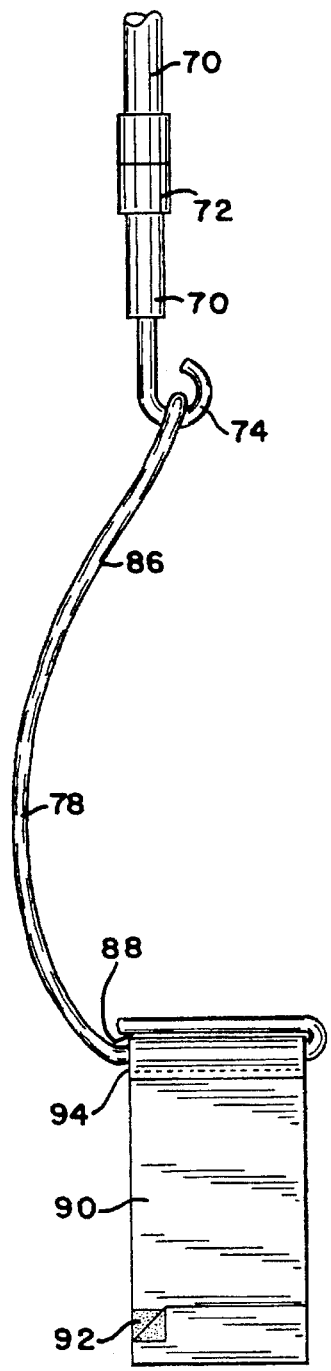
FIG. 1
FIG. 2

THERAPEUTIC TENSION APPLYING TRAVEL AID APPARATUS ATTACHABLE TO A SEAT

FIELD OF THE INVENTION

The present invention relates in general to orthopedic devices and more particularly to a device mounted to or above the seat or the like of a vehicle for applying tensile stress on a persons neck and spine while traveling.

BACKGROUND OF THE INVENTION

Traction devices for applying a prolonged pulling or tensile stress on muscles, organs, bones, or the like to correct dislocation, relieve pressure, and other therapeutic purposes have been in general use for a long time. It is common for such traction to be applied under a person's head to treat cervical or spinal fractures by applying a longitudinal force to the person's head directed away from his body resulting in a tensile stress on his back and spine a conventional apparatus for applying such traction includes a strap or pad placed under the person's jaw or chin and may include another strap or pad placed under the back of the head adjacent the neck, with means for applying a longitudinal force on those pads, tending to pull the head in a longitudinal direction away from the body.

These devices while functional for their intended use are not designed for use in combination with a seat, such as in a vehicle, train, boat, plane etc., while traveling. Furthermore, these devices do not provide means for an adjustable break-a-way attachment which in the event of an accident or the like, would allow the apparatus to disengage the pad or chin strap from the supporting structure.

An exemplary apparatus disclosed in prior art U.S. Pat. No. 4,603,689 provides an apparatus attachable to a chair. However, when the user assumes a seated position within the chair and tightens a lap belt so as to secure the lower thoracic area of the body, the apparatus when positioned may apply traction to the lower spinal region by pulling the entire body upwardly from the chair such that the weight of the entire body is substantially wholly supported by the belt.

Many other attempts to provide traction for the neck and spine are disclosed in U.S. Pat. Nos. 4,869,240, 3,759,255, 3,835,847, 3,750,658 all of which teach traction means for a person while standing or sitting while U.S. Pat. No. 4,220,147 provides a traction apparatus for use when lying down. As noted above these devices are functional but do not include the unique and advantageous qualities as taught within the present invention.

Therefore, it is contended by the applicants that a need exists for a device which may relieve the stress and strain on the neck and spinal area when riding in and/or driving a vehicle such as an automobile, truck, bus airplane etc., with its primary function being to support the weight of the head of a person without impairing their vision, their natural human body rotational mobility and/or driving skills. Furthermore, the supporting rope or cable should include means to break-a-way from its support structure when a predetermined amount of tension is exceeded such as in the case of an accident so as to allow the user a tangle-free and unobstructed exit. Such a device and/or apparatus has not been taught heretofore.

SUMMARY OF THE INVENTION

It is therefore a primary object of the present invention to provide means to support the weight of the head of an occupant of a vehicle while traveling in such a manner as to relieve stress and strain on the neck and/or spinal area of the user.

It is a further object of the present invention to provide a support means which is adjustable in a forward and reverse manner at substantially a 90 degree angle to the back of a seat occupied by the user.

Still another object is to provide support means which is adjustable in height in relation to a plane formed by the bottom of the seat.

Still another object is to provide an adjustable attachment bar which is attached in a secure manner to the base of the support means and also includes adjustment holes which capture and retain a tubular grasping arm, whereby allowing the arm to grasp a variety of different shaped chairs having variable widths and depths.

A further important object is to provide the afore mentioned grasping arm with a first and second member which slidably engage one within the other and also provides means to lock the arm members in a desired location.

Still another object is to provide a rubber sleeve on the grasping arm to protect the cover of the chair.

Yet another object is to provide a rope guide so as to discourage the weight means from swinging when the vehicle is in motion.

Still another object is to provide in a second embodiment means t attach the rope, the break-a-way and a hook to an above flat surface such as a ceiling if the user so desires.

Yet another important object is to provide a variable, adjustable tension device substantially comprising; a support structure, one or multiple pulleys, a rope or cable, means to attach variable weight, means to attach a head piece and a chin, strap for applying controlled pressure on the neck and spinal area of the occupant.

Another most important object is to provide a head stall which is of a unique shape and design so as to allow the user full natural human body rotational mobility and full unobstructed vision.

Yet another object is to provide means to attach a head stall and chin strap in combination such as disclosed in the prior art or allows for the attachment of the unique head stall of the design herewith disclosed.

Still another object is to provide the user with means to attach any optimum weight of choice, such as a bag of water, rocks, sand or the like for variable traction tension.

It is a further object to provide means to attach the adjustable tension device described above to the support structure and/or supporting surface.

Yet another object is to provide the rope or cable with a device known as a break-a-way conveniently placed so as to allow the rope or cable to separate in the event of an accident thereby relieving the tension and eliminating any possible entanglement of the user and the tension applying apparatus.

Still another object of the present invention is to provide variable adjustments for individual comfort for various sized users.

Yet another object is to provide an apparatus as disclosed herein which is portable.

Other objects and advantages will become apparent when taken into consideration with the following drawings and specifications.

BRIEF DESCRIPTION OF THE DRAWINGS

FIG. 1 is a perspective view of the apparatus shown attached to a seat and the headstall shown supporting a human head.

FIG. 2 is a side view of the headstall and chin strap when attached to a hook and break-a-way means.

DETAILED DESCRIPTION OF THE DRAWINGS

Figure 3:
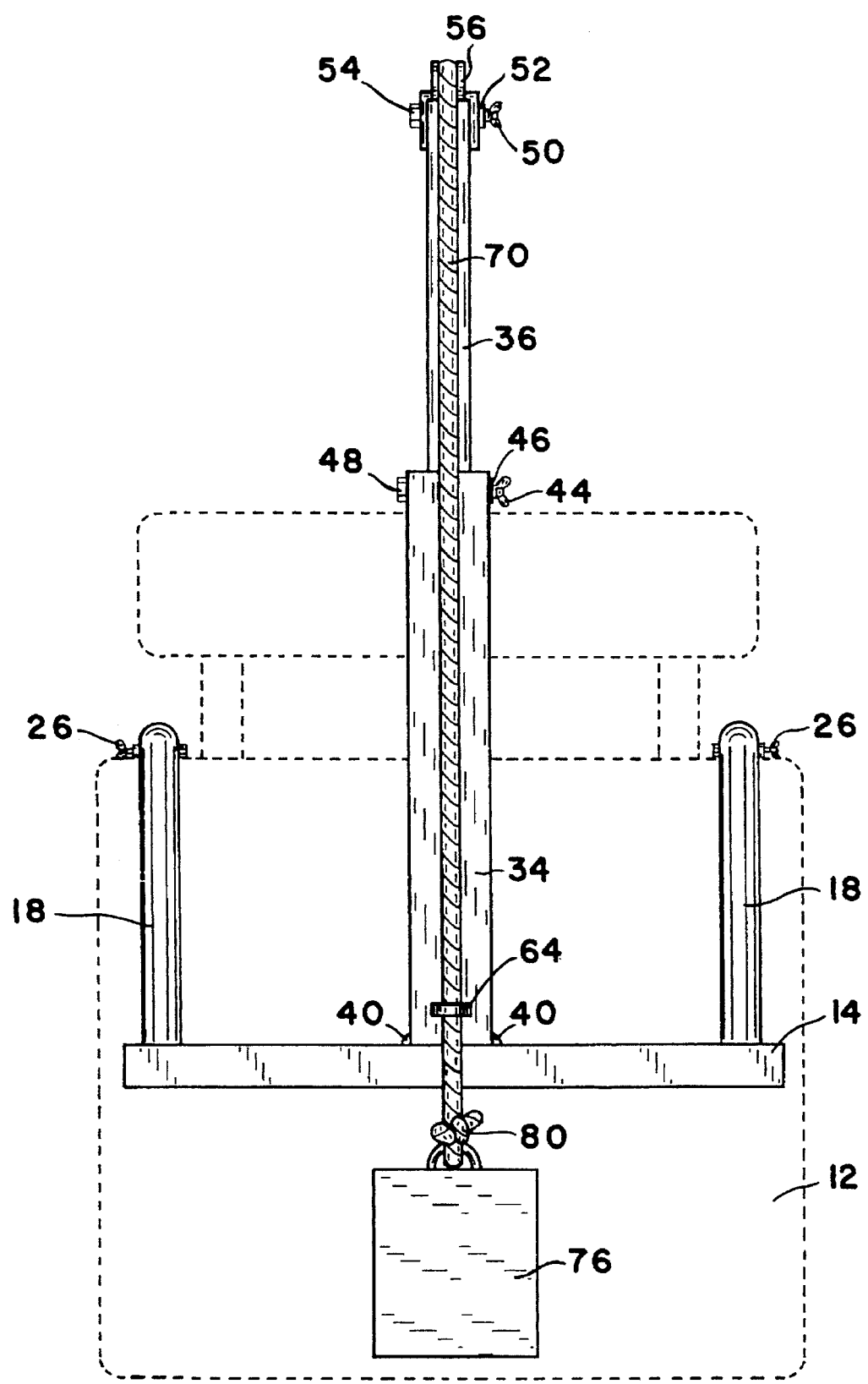
FIG. 3 is a backside view of the apparatus when attached to a seat.
Figure 6:
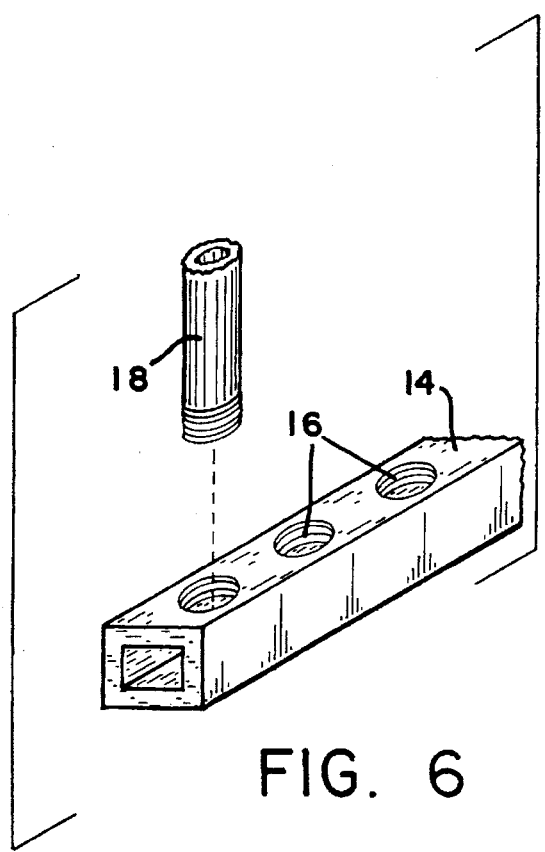
FIG. 6 is a perspective plan view of an attachment bar which shows variable attachment holes.

Shown in FIG. 1, is an arrow 10 which represents an overview of the apparatus. Shown in FIGS. 1 and 3, is a typical seat 12 (shown in ghost lines) which has a back and a sitting surface such as used in automobiles, airplanes, trains, etc. Shown in FIGS. 3 and 6, is an attachment bar 14 which is made of any suitable material such as wood, plastic, metal, etc. and may take any suitable shape of engineering choice such as an elongated, square, hollow bar having a top portion, as shown in the preferred embodiment. Attachment bar 14 is attached to the backside of seat 12 by a suitable attachment means such as multiple threaded vertical bores 16 through the top portion and positioned substantially near the ends of attachment bar 14, as shown in FIG. 6. Bores 16 are of a shape and size to receive and accept a pair of attachment arms 18. Attachment arms 18 are made from any suitable material such as wood, plastic, or moldable aluminum and are of a shape and size to grasp and capture seat 12 therewithin such as an upside down U-shape and may be one continuous arm or may include a first member 20 and a second member 22 as shown in FIG. 1. Members 20 and 22 each have a first and second end. The first end of member 20 is of a shape and size to threadably engage vertical bores 16, while its second end is of a shape and size to accept and receive the first end of member 22 so as to provide a slidable relationship for member 22 within member 20 and the members are adjustably locked together by a suitable means such as multiple screw holes 24, which are of a shape and size to accept screw 26 and are secured by washer 28 and nut 30. The second end of member 22 is of a shape and size to accept a protective sleeve 32 so as to protect seat 12 from damage.

A support means is shown in FIGS. 1 and 3, which may be made of any suitable material such as wood, plastic, metal, etc. and includes a first support member 34, a second support member 36 and a third support member 38. Members 34, 36, and 38 may be of any suitable size and shape, however, as shown in the preferred embodiment, members 34 and 38 are substantially shaped into an elongated, square, hollow member formed into an upside down "L." Each of the support members 34, 36 and 38 have a first end, a second end, a length, sides and a perimeter, while members 36 and 38 each have a top and member 34 has a back. The first end of member 34 is attached to the top portion of bar 14 by suitable means such as welding 40, or the like as shown in FIG. 3. The second end of member 34 and the first end of member 38 have their perimeter larger than the perimeter of the first and second ends of member 36 so as to allow the first end of member 36 a slidable relationship within the second end of member 34 and the second end of member 36 has a slidable relationship within the first end of member 38. The second end of member 34 and the first end of member 38 include vertical locking means such as multiple horizontal screw holes 42 which are of a shape and size to accept and receive a screw 44 and is held in a secure manner by washer 46 and nut 48, which allow for various height adjustments. The second end of member 36 and the first end of member 38 include horizontal locking means such as multiple horizontal screw holes 48 which are of a size and shape to accept and receive a screw 50 and is held in a secure manner by washer 52 and nut 54, which allows various width adjustments. The top of members 36 and 38 include means to attach a first pulley 56 and a second pulley 58 such as by a bracket 60 which attaches pulleys 56 and 58 in a secure manner.

Member 38 includes an end plate 62 on its second end which is suitably attached by means such as welding (not shown) or the like. A first cable guide 64 is attached to the back of member 34 which guides the cable but also serves as a securing means so that when the apparatus is used in a moving vehicle, the cable will not swing about. A second cable guide 66 is attached to the top of member 38 while a third cable guide 68 is attached to the end plate 62 by suitable attachment means such as screws or the like (not shown).

A cable system is provided which includes a cable 70, a break-a-way means 72, a hook 74, a weight means 76, and a headstall 78. Cable 70 may be made of any suitable material such as cotton, nylon, metal, or the like and has a first end, a second end, a first stop means 80, and a second stop means 82, such as a knot. Break away 72 (such as produced by Triple Seven Ind. of Sparks, Nev. part #777-R-100) is attached to the cable 70 at a position of engineering choice between the first and second ends of cable 70.

Figure 5:
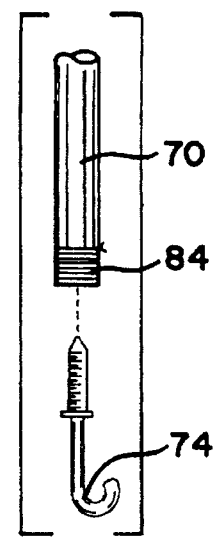
FIG. 5 is a side plan view showing means to attach a cable and hook.

The second end of cable 70 is attached to hook 74 by any suitable means such as a threaded hook threadably engaged into the second end of cable 70 and then secured by nylon wrapping 84, or the like as shown in FIG. 5. Hook 74 is of a size and shape to releasably attach any suitable headstall or apparatus, such as headstall 78 as shown in FIG. 2. Headstall 78 includes an elongated member 86 which can be made from any suitable material such as metal or the like and is formed into substantially the shape of an upside down "U" with its legs being turned upward, outwardly and folded upon itself forming space 88. Space 88 is of a shape and size to accept a chin strap 90 which is made from a suitable material such as elastic, or the like and is substantially a pair of elongated sections which are adjustably, variably connected by closure means such as VELCRO 92, while the opposite ends are folded over and secured by stitching, or the like, forming pocket 94. Pocket 94 is of a shape and size to stretch over the folded legs of member 86 and positioned in a secure manner within space 88. Headstall 78 is of a shape and size to receive and support the weight of the human head. The weight means 76 as shown in FIG. 3, may be any suitable weight such as rocks, water, sand, etc. and is removably attached to the first end of cable 70 by a suitable means such as by first stop means 80.

It will now be seen that when a human assumes a sitting position upon the sitting surface of seat 12 and then positions their head within the headstall 78 so as to allow the headstall to receive and support the weight of their head and due to the fact that the weight means has a weight, the weight means 76 therefore provides a first directional pulling force which causes second stop means 82 to engage third cable guide 68 so as to limit the first directional pulling force. A second directional pulling force is provided by the human body due to their weight and strength and when the second pulling force exceeds the first pulling force, the second pulling force causes the first stop means 80 to engage the first cable guide 64 so as to limit the second pulling force. The break away means has a pre-determined tension and when the second pulling force exceeds this pre-determined tension, such as in the case of an accident, the break away means allows the cable 70 to separate; It will now be seen that the cable system, the support means, the headstall and the human head in combination apply tension to the neck and back of the human.

Figure 4:
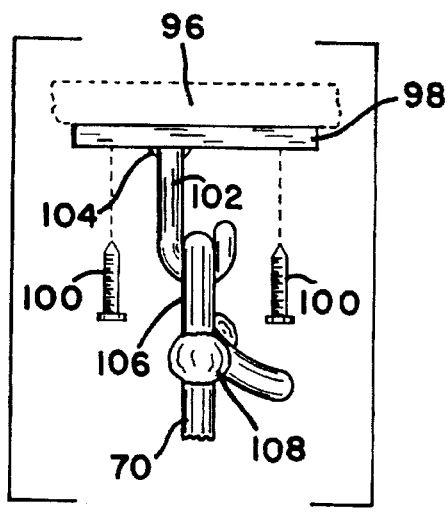
FIG. 4 is a side view of a 'second embodiment in which the cable is attached to a supporting surface as shown in ghost lines.

In FIG. 4 a second embodiment is shown attached to mounting surface 96. The mounting surface 96, such as being a ceiling within a vehicle. An attachment plate 98 may be attached to mounting surface 96 by any suitable means such as mounting screws 100. An attachment means such as hook-shaped member 102 is attached to plate 98 by a suitable means such as welding 104. Cable 70 includes a loop 106 which is of a shape and size to be positioned over hook-member 102 and therefore held in a secure manner and loop 106 is secured by knot 108. As will now be seen, when this embodiment is preferred, the user simply adjusts the length of cable 70 after determining a desired position, secures cable 70 to hook-shaped member 102 by forming loop 106 and tying knot 108, attaches headstall 78 to hook-shaped member 102 and positions his/her head within headstall 78 and adjust the chin-strap 90 until the user is comfortable and secure; This embodiment provides the user with an adjustable therapeutic tension applying apparatus.

The foregoing, specification provides a therapeutic tension applying apparatus which may be attached to a vehicle seat as shown in the preferred embodiment, or attached to a mounting surface as shown in a second embodiment, and as shown in both embodiments, the apparatus includes a break-a-way means which has a pre-determined tension which allows the cable to separate so as to allow the apparatus to be used in a vehicle without any danger of the user being injured such as in the case of an accident.

Although the invention has been shown and described in what is conceived to be the most practical and preferred embodiments, it is recognized that departures may be made therefrom within the scope and spirit of the invention, which is not be limited to the details disclosed herein but is to be accorded the full scope of the claims so as to embrace any and all equivalent devices and apparatus.

Having described our invention, what we claim and wish to secure by Letters Patent is:

1. A human therapeutic tension applying apparatus comprising: headstall means adapted to receive and support a user's head; a mounting surface; a cable; said cable having a first end and a second end, said first end being removably attachable to said mounting surface, said second end being removably attachable to said headstall; and break-a-way means, said break-a-way means having a predetermined tension and disposed intermediate said first end and second ends of said cable allowing said first and second ends of said cable to separate from each other when a pulling force on said cable exceeds said predetermined tension.

2. The apparatus of claim 1 in which said mounting surface is the interior ceiling of a vehicle.

* * * * *